(12) United States Patent
Shahidi et al.

(10) Patent No.: US 8,801,183 B2
(45) Date of Patent: Aug. 12, 2014

(54) ASSESSMENT OF MICROVASCULAR CIRCULATION

(75) Inventors: Mahnaz Shahidi, Northbrook, IL (US); Justin Wanek, Chicago, IL (US); Bruce Gaynes, Maywood, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 13/512,218

(22) PCT Filed: Nov. 30, 2010

(86) PCT No.: PCT/US2010/058349
§ 371 (c)(1),
(2), (4) Date: Oct. 22, 2012

(87) PCT Pub. No.: WO2011/066546
PCT Pub. Date: Jun. 3, 2011

(65) Prior Publication Data
US 2013/0070201 A1    Mar. 21, 2013

Related U.S. Application Data

(60) Provisional application No. 61/264,917, filed on Nov. 30, 2009.

(51) Int. Cl.
*A61B 3/14*        (2006.01)
(52) U.S. Cl.
CPC ........................................ *A61B 3/14* (2013.01)
USPC ............................................ 351/206; 351/209
(58) Field of Classification Search
USPC ........... 128/922; 382/128; 600/453, 301, 318, 600/399, 400, 410; 378/98, 98.5, 98.8; 351/206–221
See application file for complete search history.

(56) References Cited

U.S. PATENT DOCUMENTS

| 4,998,533 A | 3/1991 | Winkelman |
| 5,196,873 A | 3/1993 | Yamanobe et al. |

(Continued)

FOREIGN PATENT DOCUMENTS

| RU | 2320305 C1 | 3/2008 |
| WO | 97/15229 A1 | 5/1997 |
| WO | 01/22741 A2 | 3/2001 |

OTHER PUBLICATIONS

Christopher G. Owen, Timothy J. Ellis, Alicja R Rudnicka and E. Geoffry Woodward; OPtimal Green (red-free) digital imaging of conjuctival vasculature;Opthial. Physiol. Opt; 2002; 22; 234-243.*

(Continued)

*Primary Examiner* — Ricky Mack
*Assistant Examiner* — Robert E Tallman
(74) *Attorney, Agent, or Firm* — Nutter McClennen & Fish LLP

(57) ABSTRACT

Methods and compositions are disclosed to quantitatively measure in vivo blood vessel diameter, blood velocity, and other flow dynamics. Such methods and compositions can optimize therapeutic interventions designed to prevent or reduce the risk of cardiovascular and blood disorders. In one aspect, the methods and apparatus involve calculating blood vessel characteristics from a two dimensional image of a blood vessel in the conjunctiva of a subject's eye. In another aspect, a series of temporal images of a blood vessel are obtained to determine blood flow properties. The apparatus can include, for example, a biomicroscope, an illuminating light source and a high speed camera to acquire the series of temporal images with the data then analyzed by a programmed processor.

15 Claims, 11 Drawing Sheets

(56) References Cited

U.S. PATENT DOCUMENTS

| | | | |
|---|---|---|---|
| 5,357,550 | A | 10/1994 | Asahina et al. |
| 5,410,376 | A | 4/1995 | Cornsweet et al. |
| 5,481,622 | A | 1/1996 | Gerhardt et al. |
| 5,956,125 | A | 9/1999 | Rosse et al. |
| 2002/0058874 | A1 | 5/2002 | Ono et al. |
| 2003/0050553 | A1 | 3/2003 | Samoszuk et al. |
| 2004/0189939 | A1 | 9/2004 | Dick et al. |
| 2005/0288564 | A1 | 12/2005 | Iuliano |
| 2006/0161063 | A1* | 7/2006 | Shau ............................ 600/504 |
| 2008/0089480 | A1 | 4/2008 | Gertner |
| 2009/0030144 | A1 | 1/2009 | Mizutani et al. |
| 2009/0149726 | A1 | 6/2009 | Hyde et al. |
| 2010/0027857 | A1* | 2/2010 | Wang ............................ 382/128 |
| 2010/0104168 | A1* | 4/2010 | Dobbe ........................... 382/134 |

OTHER PUBLICATIONS

Cheung et al., Correlation of abnormal intracranial vessel velocity, measured by transcranial Doppler ultrasonography, with abnormal conjunctival vessel velocity, measured by computer-assisted intravital microscopy, in sickle cell disease. Blood. Jun. 1, 2001;97(11):3401-4.

Cheung et al., Microvascular abnormalities in sickle cell disease: a computer-assisted intravital microscopy study. Blood. Jun. 1, 2002;99(11):3999-4005.

Duench et al., Assessment of variation in bulbar conjunctival redness, temperature, and blood flow. Optom Vis Sci. Jun. 2007;84(6):511-6.

Ellis et al., Determination of red blood cell oxygenation in vivo by dual video densitometric image analysis. Am J Physiol. Apr. 1990;258(4 Pt 2):H1216-23.

Ellis et al., Application of image analysis for evaluation of red blood cell dynamics in capillaries. Microvasc Res. Sep. 1992;44(2):214-25.

Embury et al., In vivo blood flow abnormalities in the transgenic knockout sickle cell mouse. J Clin Invest. Mar. 1999;103(6):915-20.

Gruen, A.W., Adaptive least squares correlation: A powerful image matching technique. S Afr J Photogramm, Remote Sensing Cartography. 1985;14(3):175-187.

International Search Report and Written Opinion mailed Feb. 11, 2011 for Application No. PCT/US2010/058349 (7 pages).

Japee et al., Automated method for tracking individual red blood cells within capillaries to compute velocity and oxygen saturation. Microcirculation. Sep. 2005;12(6):507-15.

Koutsiaris et al., Volume flow and wall shear stress quantification in the human conjunctival capillaries and post-capillary venules in vivo. Biorheology. 2007;44(5-6):375-86.

Schaser et al., Noninvasive analysis of conjunctival microcirculation during carotid artery surgery reveals microvascular evidence of collateral compensation and stenosis-dependent adaptation. J Vasc Surg. Apr. 2003;37(4):789-97.

Shahidi et al., Quantitative assessment of conjunctival microvascular circulation of the human eye. Microvasc Res. Mar. 2010;79(2):109-13. Epub Jan. 4, 2010.

Startseva et al., The diagnosis of transcapillary flow disturbances in the lungs of lung cancer. Clin Hemorheol Microcirc. 2006;35(1-2):305-6.

International Preliminary Report relating to International Applicatiaon No. PCT/US2010/058349 dated Jun. 14, 2012.

European Search Report for Application No. 10834036.5, issued Feb. 7, 2014. (10 Pages).

* cited by examiner

ASSESSMENT OF MICROVASCULAR CIRCULATION

GOVERNMENT SPONSORSHIP

This invention was made with government support under EY17918 and EY01792 awarded by the National Eye Institute. The government has certain rights in the invention.

REFERENCE TO RELATED APPLICATION

The present application claims priority to a provisional application entitled "Methods for Assessing Conjunctival Hemorheology of the Human Eye" filed on Nov. 30, 2009 and having Ser. No. 61/264,917, which is herein incorporated by reference.

TECHNICAL FIELD

The invention relates to methods and apparatus for measuring blood flow and blood flow dynamics in microvasculature.

BACKGROUND OF THE INVENTION

Hemorheology, the study of the flow properties of blood, has great potential for early detection or diagnosis of many illnesses, such as thromboembolisms, stroke, hyperocoagulability syndromes and blood diseases like sickle cell anemia. However, it is broadly recognized that ex vivo examination of human hemorheology, e.g., by studying blood samples, provides only limited data and typically cannot accurately characterize in vivo human circulatory conditions. Likewise, in-situ, non-invasive measurements of human hemorheology also pose challenges in accurately describing the rheological parameters of blood flow. For example, in vivo imaging is hindered by difficulties in tissue accessibility and mechanistic validity of the technology.

Ideally, hemorheological imaging should be conducted on tissue sources representative of critical organ systems, e.g., the human brain, in a manner whereby microvascular arteriolar and venular networks can be accessible within a transparent medium to allow non-invasive in vivo imaging. There exists a need for better methods and apparatus for conducting such imaging and for translating acquired image data into hemorheological measurements that can predict or diagnose thromboses, blood disorders and the like.

SUMMARY OF THE INVENTION

Methods and apparatus are disclosed for non-invasive measurement of blood flow properties in target tissue by obtaining a series of temporal images of a blood vessel and calculating blood flow properties and/or blood vessel characteristics from the series of time lapsed images. For example, a system employing a biomicroscope, an illuminating light source and a high speed camera can be used to acquire the series of temporal images with the data then analyzed by a programmed processor.

In one aspect of the invention, the target tissue is the thin mucous membrane that covers the sclera of the human eye, the conjunctiva. The eye and brain have several notable parallels that from a hemorheologic standpoint are distinctive in terms of human anatomy. The eye and at least a portion of the brain are supplied by branches of the internal carotid artery that when studied from a physical perspective results in similar microcaliber size vessels at equidistance from the main vessel branching tree, with corresponding parallels in hydraulic fluid dynamics. Therefore, measurements of blood pressure and rheological components of blood flow in the arteriolar and/or venular capillary beds of the eye can provide valuable insights into the hemorheology of at least portions of the cerebral cortex. Furthermore, the eye is compartmentalized into a singular unit within the skull that is subject to the same external and physical internal force of the cerebral cortex.

It has been discovered that the blood flow characteristics of the human eye do indeed parallel those of the cerebral circulation, providing a succinct portrayal of vascular hemodynamics as well as alterations due to disease and therapeutic interventions. Specifically, accessibility of the eye, notably the bulbar conjunctival microvasculature, can be utilized to assess and optimize the use of various pharmacotherapeutic interventions designed to prevent or reduce the risk of cerebral vascular disease and stroke. In one embodiment, a method based on slit lamp biomicroscope digital imaging in conjunction with spatial temporal image analysis techniques is disclosed to quantitatively measure the human eye conjunctiva blood vessel diameter, velocity, and flow rate.

In one aspect of the invention, a method is disclosed for determining blood velocity in a target tissue by acquiring a series of temporal frames with registered images of at least one vessel in the target tissue, identifying at least one blood cell present in each of a plurality of frames; and calculating blood velocity within the vessel based on a distance travelled by the blood cell in the vessel between frames. Preferably, the target tissue is a conjunctiva of an eye.

The method can be practiced by acquiring a series of image frames at least 30 Hz, 40 Hz, 50 Hz, 60 Hz, 80 Hz or 100 Hz. Preferably the method is practiced with apparatus that compensates for target movement by tracking eye movements. The method can further include enhancing acquisition of blood vessel images by illuminating the target tissue with light having a wavelength in a range of about 500 nm to 560 nm.

The method can further include determining blood flow in the blood vessel by obtaining a series of temporal two-dimensional image of the vessel in the target tissue; generating a spatial-temporal image for extracting blood velocity data; determining dimensions of the vessel from the two-dimensional image; and calculating blood flow within the vessel based on blood cell velocity and blood vessel dimensions.

In another aspect of the invention, a non-invasive method is disclosed for predicting or detecting blood flow abnormalities in a subject by obtaining blood flow properties within at least one conjunctival vessel in a first eye of a subject, obtaining blood flow properties within at least one conjunctival vessel in a second eye of a subject and comparing the measurements from the two eyes, wherein a difference in blood flow dynamics between the two eyes is an indicator of blood flow abnormalities.

In yet another aspect of the invention, a hemodynamics measurement apparatus is disclosed having a light source configured to project radiation onto a target tissue, optics configured to image at least one vessel in the tissue, a detector to capture a series of temporal images of the vessel; and a processor to calculate blood flow dynamics in the vessel from the series of images. The apparatus further comprises a slit lamp biomicroscope and can be configured to image blood vessels in the conjuntiva of a subject's eye.

The apparatus can further include a white light source or laser that generates light of at least one wavelength in the range of about 450 to 600 nm, e.g., a broadband light source with an appropriate filter. Preferably, the light source generates light at a wavelength in a range from about 500 nm to about 600 nm or in a range from about 500 nm to about 560 nm to image blood vessels in the conjunctiva of the subject's eye. The apparatus can further include an eye tracking mechanism that compensates for movement of the eye from one temporal image to another. For example, the eye tracking mechanism is configured to detect changes in pupil position.

The detector of the apparatus can further include a camera, e.g., a charge-coupled device (CCD) camera to acquire two-dimensional images, and a camera controller configured to acquire a plurality of images over a time interval at a frame rate of at least 30 Hz, 40 Hz, 50 Hz, 60 Hz, 80 Hz or 100 Hz.

In one embodiment, the apparatus can be stationary and provide the subject with a headrest and chin rest to align the target tissue and includes image acquisition optics. In another embodiment, the apparatus can be a handheld apparatus. The apparatus can further include a fixation light source to assist the subject in maintaining a steady gaze during image acquisition.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

DETAILED DESCRIPTION

Figure 1:
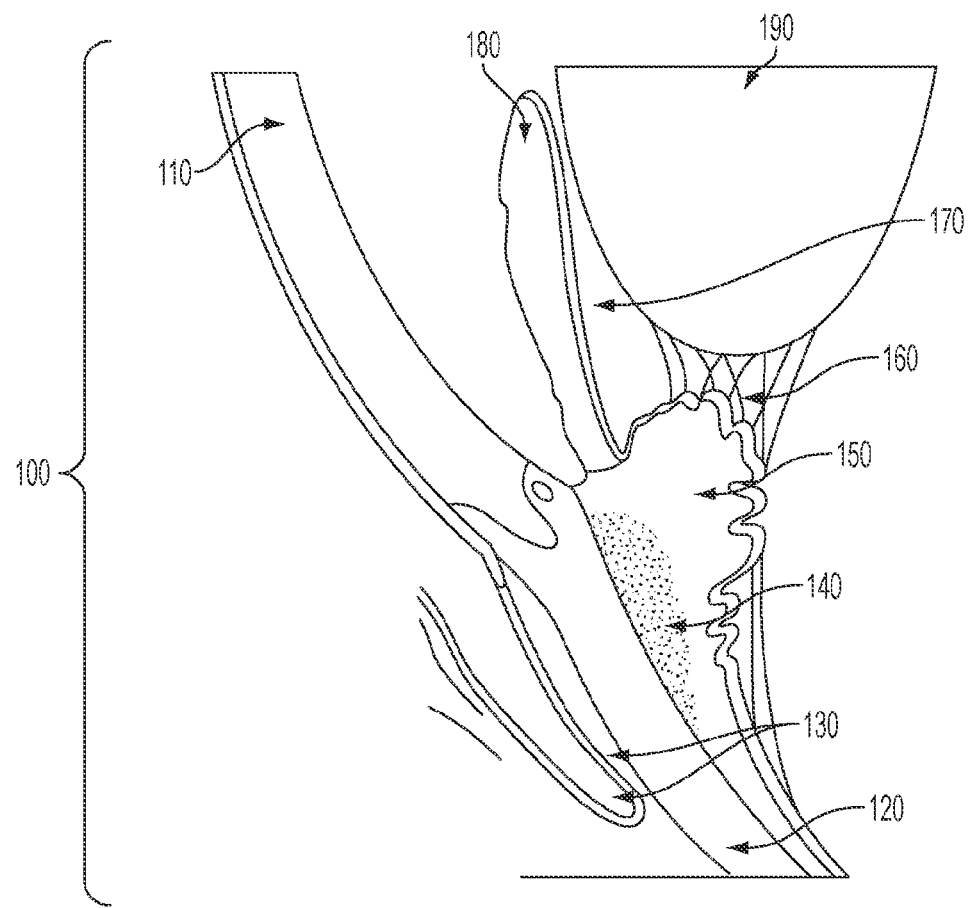
FIG. 1 is a schematic illustration of the tissue layers of the eye.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

All publications, patents and patent applications cited herein, whether supra or infra, are hereby incorporated by reference in their entirety. As used in this specification and the appended claims, the singular forms "a," "an," and "the" include plural references unless the content clearly dictates otherwise. The terms used in this invention adhere to standard definitions generally accepted by those having ordinary skill in the art. In case any further explanation might be needed, some terms have been further elucidated below.

The term "subject" as used herein refers to any living organism in which an immune response is elicited. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

Assessment of blood flow is important for the diagnosis and understanding of many diseases. Technologies that provide in vivo quantitative assessment of blood flow dynamics are needed to supplement knowledge of required blood supply to the cerebral cortex, as well as, providing better methods of diagnosing and monitoring development of vascular and blood disorders.

The methods and apparatus for spatial-temporal image (STI) generation and axial velocity data extraction differ from previous studies. The STI can be created based on intensity values along the vessel centerline and axial velocity was determined as the average slope of the lines fitted to the prominent bands in the STI. Moreover, the methods and apparatus can utilize multiple sequential image frames for deriving reliable blood velocity measurements to assess and monitor development or progression of vascular and blood disorders.

Arterial disease is a multifactorial disease that results in the deposition of atheromatous plaque and progressive luminal narrowing of the arteries. The atherosclerosis process involves lipid induced biological changes in the arterial walls resulting in a disruption of homeostatic mechanisms that keeps the fluid phase of the blood compartment separate from the vessel wall. The luminal narrowing or blockage results in reduced ability to deliver oxygen and nutrients to the heart muscle and other parts of the body, producing ischemic stroke and/or myocardial infarction and sudden death as a result. Though blood supply may be cut off suddenly due to an arterial blockage, occlusion usually progresses slowly.

A key problem in treating vascular diseases is proper diagnosis. Often the first sign of the disease is sudden death. For example, approximately half of all individuals who die of coronary artery disease die suddenly. Furthermore, for 40-60% of the patients who are eventually diagnosed as having artery disease, ischemic stroke and/or myocardial infarction is the first presentation of the disease. Unfortunately, approximately 40% of those initial events go unnoticed by the patient. It is now believed that, identification and stabilization of vascular diseases is an important element in the treatment of vascular diseases.

Methods of diagnosing and/or monitoring development of blood disorders are also of great importance. Diabetic retinopathy is a progressive degeneration of retinal blood vessels and is a consequence of diabetes, in particular, diabetes mellitus. One important aspect of the disease is retinal edema. Fluid buildup from deteriorating blood vessels and capillaries causes edema. As the disease progresses, the damage proliferates and large hemorrhages and retinal detachment can result.

The term "retinopathy" also refers to noninflammatory degenerative diseases of the retina. The methods of the present invention encompass retinopathy or a visually-related disease that is characterized by one or more of the following retinal signs: capillary obstruction, nonperfusion, leukostasis, formation of vascular lesions and/or proliferation of new blood vessels in association with ischemic areas of the retina. Leukostasis refers to the stasis or non-movement of white blood cells (e.g., leukocytes) in the vasculature. Other disorders or diseases implicated by the invention involve diseases which result in retinal edema and/or retinal ischemia.

Capillary occlusions constitute a characteristic pathologic feature in diabetic retinopathy, and, when widespread, initiate neovascularization. Neovascularization (e.g., angiogenesis) refers to the formation or growth of new blood vessels. Microaneurysms, intraretinal microvascular abnormalities and vasodilation also are commonly found in early stages of diabetic retinopathy and have been correlated to capillary occlusions. (Schroder, 1991). Leukocytes cause capillary obstruction that is involved in diabetic retinopathy via two mechanisms. This obstruction is the result of the leukocytes' large cells volume and high cytoplasmic rigidity. Leukocytes can become trapped in capillaries under conditions of reduced perfusion pressure (e.g., caused by vasoconstriction) or in the presence of elevated adhesive stress between leukocytes and the endothelium, endothelial swelling, or narrowing of the capillary lumen by perivascular edema. Examples of leukocytes include granulocytes, lymphocytes, monocytes, neutrophils, eosinophils, and basophils. Elevated adhesive stress can result from release of chemotactic factors or expression of adhesion molecules on leukocytes or endothelial cells. Secondly, leukocytes injures capillaries leading to capillary death, also known as "capillary dropout."

Anemia is another condition in which blood has a lower than normal number of red blood cells. This condition also can occur if red blood cells don't contain enough hemoglobin. The body may produce too few blood cells or the blood cells may not work properly. In either case, anemia can result. Red blood cells may be faulty or decreased due to abnormal red blood cells or the lack of minerals and vitamins needed for red blood cells to work properly.

Sickle cell anemia is an inherited disease in which red blood cells form an abnormal crescent shape. The distorted red blood cells are fragile, sickle-shaped cells and deliver less oxygen to the body's tissues. They also can clog more easily in small blood vessels, and break into pieces that disrupt blood flow.

It has been recently found that optical imaging can be used to directly measure blood flow and the hemodynamic response non-invasively from the surface vessels of the human conjunctiva. Altered blood flow and/or changes in the conjunctival blood supply may also change significantly with age, states of health and effects from medication. Devices and techniques may be particularly helpful with patients who have suffered a traumatic brain injury and/or those with low blood flow states and low blood pressure.

FIG. 1 is a schematic illustration of an eye. The eye with its high transparency and surface vasculature offers an opportunity to perform vascular measurements. The measurements can be noninvasive. The front of the eye is made up of multiple tissues as illustrated in FIG. 1. Light entering the eye 100 passes through the cornea 110, iris 180, posterior chamber 170 and lens 190 of the human eye 100. Furthermore, the eye comprises multiple layers of tissue, ciliary muscle 140, ciliary body 150 and suspensory ligament 160. The eye is encompassed with a hard tissue, the sclera 120, which supplies oxygen to the eye 100.

The conjunctiva 130 covers the exposed surface of the eye, with the exception of the cornea. The conjunctiva is a clear, thin layer of tissue that lies over the white part of the eye and also lines the inside of the eyelids. The conjunctiva helps keep the eyelids and eyeball moist, and has other functions important for the eye. The human conjunctiva is a richly vascularized transparent tissue that provides both protection and lubrication to the eye and is readily accessible for examination by a variety of techniques. Being highly vascularized, the conjunctiva has been found to provide an excellent site for the non-invasive measurement of blood flow dynamics. Non-invasive methods include, but are not limited to, illumination and imaging of vessels. One embodiment is related to optical non-invasive methods to detect the presence of blood flow in the tissue of a subject by utilizing imaging of vessels in the conjunctiva. The instruments and methods of the present invention do not require direct contact of the instrument with a subject's conjunctiva in order to make the vessel measurements.

Monitoring conjunctival vessels can have significant advantages due to ease of assessment (non-invasive and efficient) as compared with other modes of assessment. A digital imaging device can capture high quality, non-mydriatic (e.g., undilated pupil), conjunctival images; can be obtained in a simple, compact design, such as a handheld device. In one embodiment, the system and method can involve a monostatic beam geometry, e.g., the light incoming to the tissue to be observed and the light collected in reflection from the tissue passing through the same location in space between the object and the optical component nearest the tissue. As a result of the monostatic beam geometry, the instrument can be focused on a surface tissue, such as the conjunctiva, therefore not requiring dilation of the eye. However, the instrument remains operative even for deeper tissues, such as the retina.

There are many benefits that accrue for non-invasive imaging and measurements of blood vessels of the eye. Dilation is generally performed by applying chemicals topically and waiting for the dilation to occur. The waiting period can be on the order of minutes, e.g., twenty minutes. Absence of a dilation requirement means that an instrument embodying principles of the invention can be used immediately, rather than only after a delay necessitated by the dilation of the pupil. This allows use in settings such as emergency or field use, where other instruments become useful only after the dilation of the pupil is complete. Dilation of the pupil causes the patient to have reduced visual acuity for periods of up to hours, until the effect of the dilation chemicals wears off. Dilation of the pupil can require a patient to use protective eyewear or to avoid light of ordinary intensity. Dilation of the pupil can cause a patient discomfort. The use of an instrument embodying principles of the methods herein can eliminate all of the above negative features of direct contact with the eye by using methods of non-invasive measurements of blood flow within the eye.

Measuring blood flow velocity, as provided herein, provides a stable baseline level of blood flow velocity. For some applications, it is desirable to measure the variability of blood flow velocity during the cardiac cycle or between different vessels.

Monitoring blood flow in different conjunctival vessels can allow for a method of predicting or detecting blood flow abnormalities that may be detectable by variations in blood flow. In one embodiment, it is desirable to measure variability of blood flow velocity and blood flow in adjacent vessels or in vessels in different eyes. In another embodiment, blood flow abnormalities, such as diabetic retinopathy, microaneurysms, intraretinal microvascular abnormalities and vasodilation, can be predicted or detected by obtaining blood flow properties and comparing them between one or more vessels or between eyes. In one embodiment, blood flow abnormalities can be predicted or detected by obtaining blood flow properties by obtaining blood flow properties within one or more blood vessels in the conjunctiva of one eye, obtaining blood flow properties within one or more blood vessels in the conjunctiva of the other eye, and comparing the measurements from the two eyes where a difference in blood flow dynamics between the two eyes is an indicator of blood flow abnormalities. The difference can be measured as at least a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95% or 100% difference in blood flow dynamics between the two eyes. In another embodiment, In one embodiment, blood flow abnormalities can be predicted or detected by obtaining blood flow properties by obtaining blood flow properties within one or more blood vessels in the conjunctiva of an eye, obtaining blood flow properties within an adjacent blood vessel in the conjunctiva of the eye, and comparing the measurements from the different vessels where a difference in blood flow dynamics is an indicator of blood flow abnormalities. The difference can be measured as at least a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95% or 100% difference in blood flow dynamics between the two vessels.

An apparatus, based on a combination of a processor and an optical imaging camera, can allow for direct monitoring, quantification, comparison and detection of blood flow parameters. Further developments to the system, for example including a handheld automated detection device, can also be embodied in the methods and systems.

Figure 2:
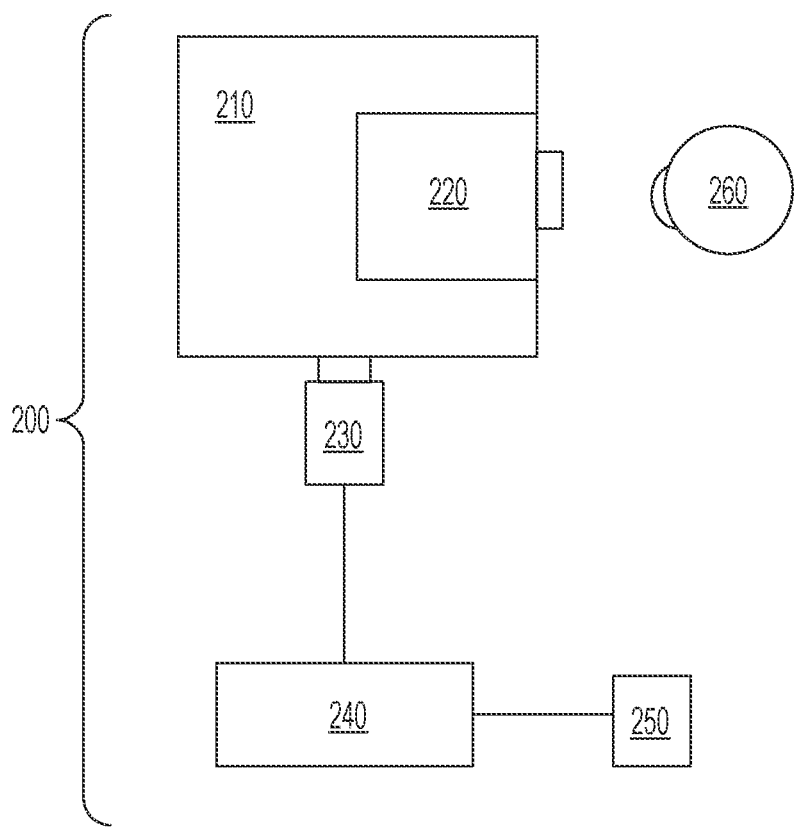
FIG. 2 is a schematic illustration of an apparatus for assessing the microvasculature according to the invention.

FIG. 2 provides a schematic view of an apparatus 200 for determining blood flow dynamics in tissue. The apparatus 200 can comprise a biomicroscope 210, light source or light illumination and optics 220 adapted to image a region of eye tissue 260, a detector 230 to capture two dimensional images of the tissue, a processor 240 for quantifying at least one property from the two dimensional images and calculating blood flow dynamics and a monitor 250 for displaying the output data.

The light source 220 can be any suitable light source or laser which can generate a suitable light for imaging purposes. The light source can be a separate light source or it can be integrated as a component of another element of the apparatus. The light source can be integrated as a component of a biomicroscope, binocular indirect ophthalmoscope or an analogous instrument known by one skilled in the art. In one embodiment, the light source can be delivered through a magnifying system designed to examine living tissue. In one embodiment, the light source can be delivered through a slit lamp biomicroscope to examine ocular tissues.

The light source 220 can generate white light or laser light, preferably light within a spectral range with wavelengths greater than about 400 nm. In one embodiment, the light source can generate light having wavelengths in a range of about 400 nm to about 900 nm. The light source can generate light having wavelengths in a range of about 500 nm to about 800 nm. The light source can generate light having wavelengths in a range of about 500 nm to about 700 nm. In another embodiment, the light source can generate light having wavelengths in a range of about 500 nm to about 600 nm. In one embodiment, the light source can generate light having wavelengths in a range of about 500 nm to about 560 nm.

In one embodiment the apparatus can further comprise a filter attached to the light source 220. The filter can filter radiation/light of specific wavelengths or a range of specific wavelengths. In a preferred embodiment, the filter allows radiation/light of wavelengths in a visible spectrum to pass through. In another embodiment, the filter allows radiation/light of wavelengths in a range of about 400 nm to about 900 nm to pass through. The filter can allow radiation/light of wavelengths of about 500 nm to about 600 nm to pass through. The filter can allow radiation/light of wavelengths of about 500 nm to about 560 nm to pass through. The filter can allow radiation/light of wavelengths of about 535 nm to about 545 nm to pass through. In yet another embodiment, the filter can be a green filter.

The optical components of the apparatus used to carry out the method are preferably configured so that energy on the eye (as well as other areas susceptible to tissue toxicity, such as the lens and cornea) transmitted from the light is not greater than 500 mW/cm$^2$, 400 mW/cm$^2$, 300 mW/cm$^2$, 200 mW/cm$^2$, 100 mW/cm$^2$, 50 mW/cm$^2$, 45 mW/cm$^2$, 40 mW/cm$^2$, 35 mW/cm$^2$, or 30 mW/cm$^2$.

The apparatus can also comprise a scanner. The scanner can deflect the radiation/light to move across a section of the tissue or capture images from a particular coordinate or set of coordinates on the tissue. Some non-limiting examples of scanners for use with the apparatus can be a galvanoscanner, a resonant mirror scanner, an acoustic optical modulator, a polygonal scanner and/or a microelectromechanical scanner. The scanner can be driven to rotate in an arc, in an oscillating motion or in a manner appropriate for illuminating a desired section of tissue. For multiple measurements, the device may be able to be configured to focus on a different eye, alternating the eye to which the light is transmitted, to reduce the amount of exposure to any one eye.

As noted above, the imaging module can also include an eye tracking mechanism. The tracking mechanism can align (move) the irradiation position even if the tissue moves during irradiation/illumination. The human eye exhibits micromovements with a frequency in the order 10 Hz. These micromovements are involuntary and it is therefore not possible for a subject to suppress these movements by will. Tracking eye movements and/or orientation is one embodiment of obtaining a high potential for accuracy. Specifically, coupling the eye tracking mechanism with a response system which provides real-time beam adjustment, so that eye movements are nullified relative to the system.

Various mechanisms are known for eye tracking. See, for example, U.S. Pat. No. 5,410,376 of Cornsweet et al. entitled "Eye Tracking Method And Apparatus," U.S. Pat. No. 5,196,873 of Yamanobe et al. entitled "Eye Movement Analysis System," U.S. Pat. No. 5,481,622 of Gerhardt et al. entitled "Eye Tracking Apparatus And Method Employing Grayscale Threshold Value," and Published U.S. Patent Application No.

US 2004/0189939 A1 of Dick entitled "Method And Device For Tracking Eye Movements," all of which are incorporated herein in the entirety.

The apparatus can further comprise detector optics 230 to capture two dimensional images. The detector optics 230 can be a biomicroscope, binocular indirect ophthalmoscope or an analogous instrument known by one skilled in the art. The biomicroscope can be designed for detailed examination of ocular tissues containing a magnifying system. One embodiment further comprises a method of tracking the movement of the eye by imaging the eye with at least one detector. The detector(s) can comprise a camera and the movement of the eye can be tracked with reference points in the eye.

In one embodiment, the detector 230 can be a camera to capture two dimensional images. The camera can be a charge-coupled device. The camera can also be an intensified or electron multiplying camera. Other examples of cameras can be used to capture the images as one skilled in the art would be familiar with. Moreover, the camera can be synchronized with the light source, scanner, and/or pulse monitor to obtain a series of temporal two-dimensional images of the tissue. Additionally, the camera can be controlled by a separate camera control device or another element of the apparatus. The camera control device can regulate the camera to acquire a plurality of images at time intervals synchronized with a pulse monitor thereby acquiring a series two dimensional images at specific time intervals during the cardiac cycle.

The apparatus can also comprise a processor 240. The processor 240 can calculate and quantify information received from two dimensional images. The processor can also control the camera by synchronizing with the scanner, pulse monitor and/or light source 220 to capture a series of temporal two-dimensional images of the tissue. Additionally, the processor 240 can have an input/output control, memory, electronic circuitry made of digital circuitry, analog circuitry, or both and can be programmable. In a preferred embodiment, the processor 240 can be a computer. The computer can have a software program to synchronize image capture rate with the light source. Additionally, the processor 240 can synchronize image capture rate with the light source and pulse monitor, to obtain a series of temporal two-dimensional images. The processor 240 can also act as a controller for the camera, scanner or any other element of the apparatus.

The processor 240 can be a computer programmed to convert the information obtained in the two dimensional images, e.g. vessel and blood cell location, to quantifiable blood flow dynamic measurements. Moreover, the computer can have a software program to convert the series of temporal two-dimensional images obtained from the camera into vessel diameter, blood velocity, blood cell dimensions, etc. In one embodiment, the process can be programmed to acquire and store temporal two-dimensional images.

In another embodiment, information can be transmitted to a remote source such as a computer, database, remote physician or the like via wireless information transfer or other connection through a suitable communication link or a computer network.

The apparatus can also comprise a monitor 250. The monitor 250 can display the data calculated by the processor 240 and/or images captured by the detector 230. The monitor can also be linked to the processor. In another embodiment, the monitor can be part of the processor.

Figure 3:
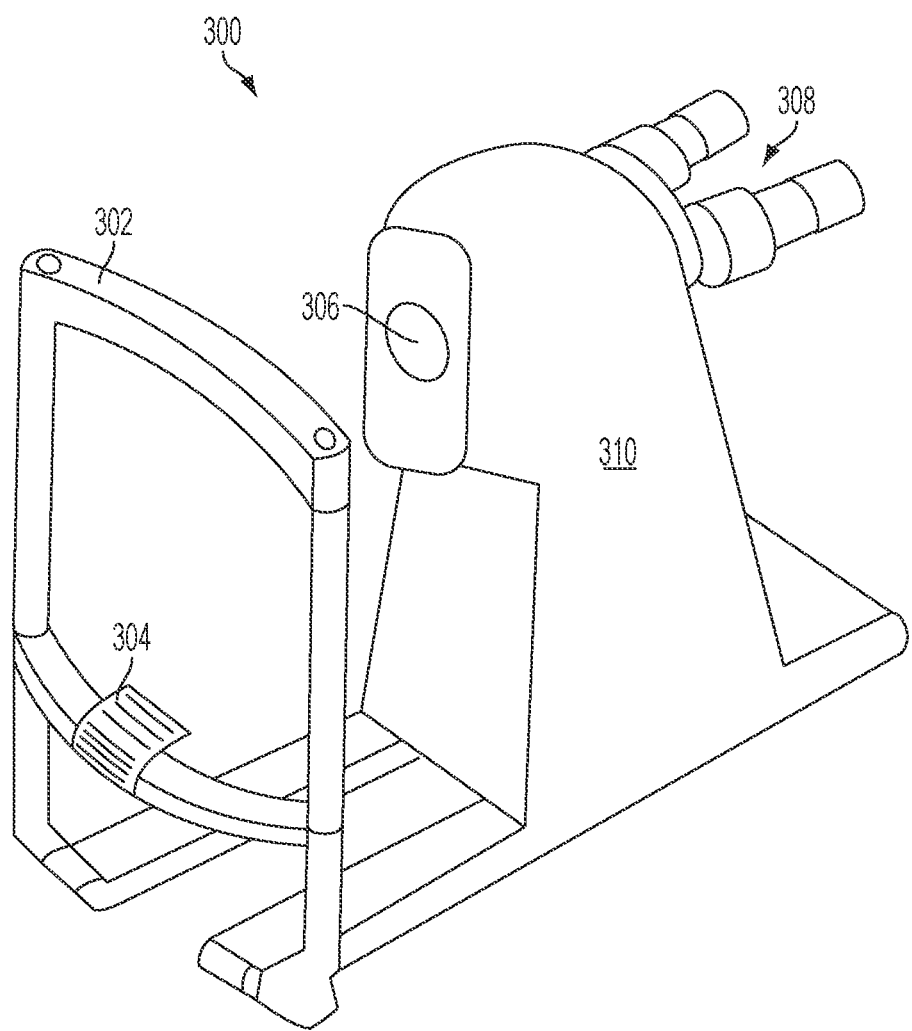
FIG. 3 is another schematic illustration of an apparatus for assessing the microvasculature of the conjunctiva.

FIG. 3 is a schematic illustration of an apparatus 300 for assessing the microvasculature of the conjunctiva including a headrest 302, chin rest 304, illumination and optics 306 and binocular eyepieces 308. Housing 310 encases the illumination source, imaging optics and camera (not shown). The images from the camera can be conveyed either by cable or by wireless connection to a processor.

Figure 4:
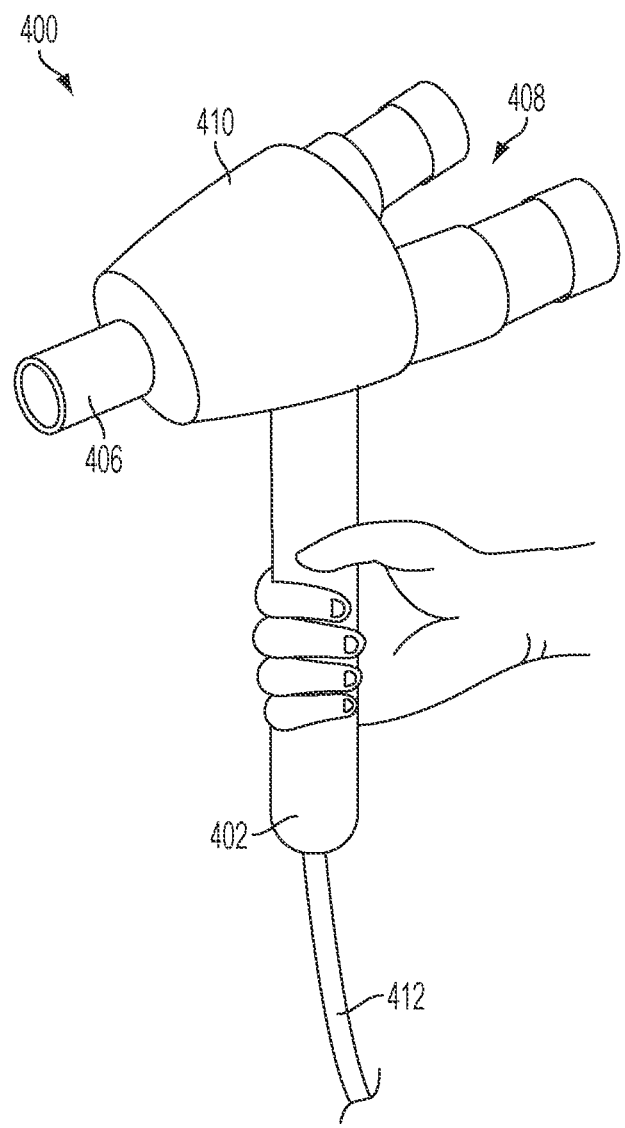
FIG. 4 is a schematic illustration of an alternative, handheld apparatus for assessing the microvasculature of the conjunctiva.

FIG. 4 is a schematic illustration of an alternative, handheld apparatus 400 for assessing the microvasculature of the conjunctiva including a handle 402, illumination and optics 406 and binocular eyepieces 408. Body 410 encases the illumination source, imaging optics and camera (not shown). Again, the images from the camera can be conveyed either by cable 412 or by wireless connection to a processor.

Figure 5:
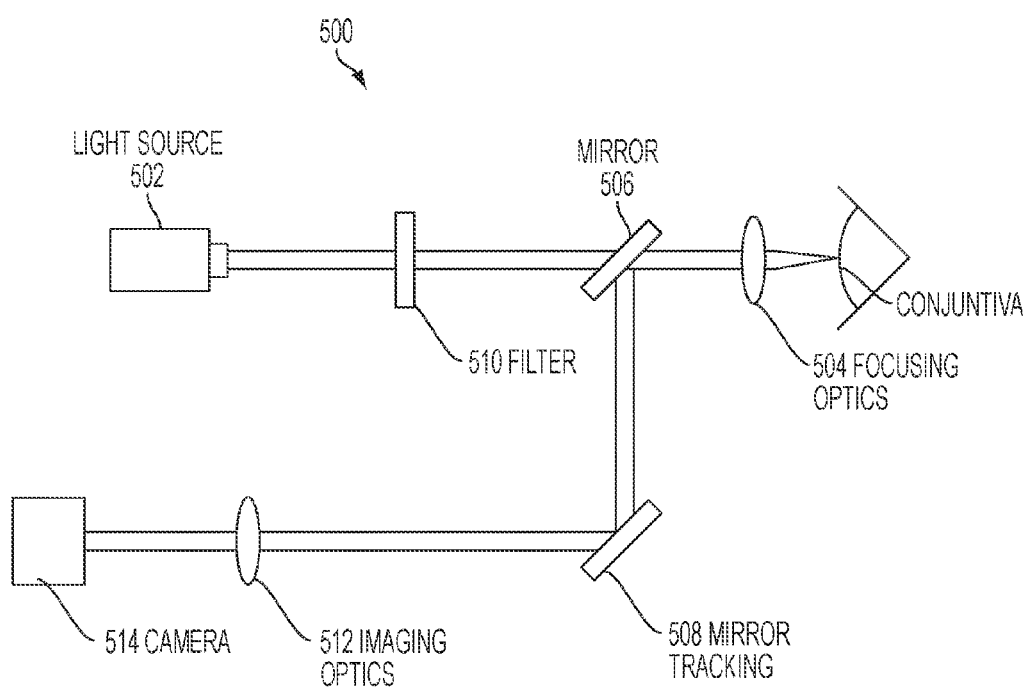
FIG. 5 is a schematic illustration of an image data acquisition module according the invention.

FIG. 5 is a schematic illustration of an image data acquisition module 500 according the invention including an illumination light source 502, focusing optics 504, a mirror 506, tracking mirror 508, filter 510, imaging optics 512 and CCD camera 514. Optionally mirror 508 is a tracking mirror capable of compensating for eye movements.

Figure 6:
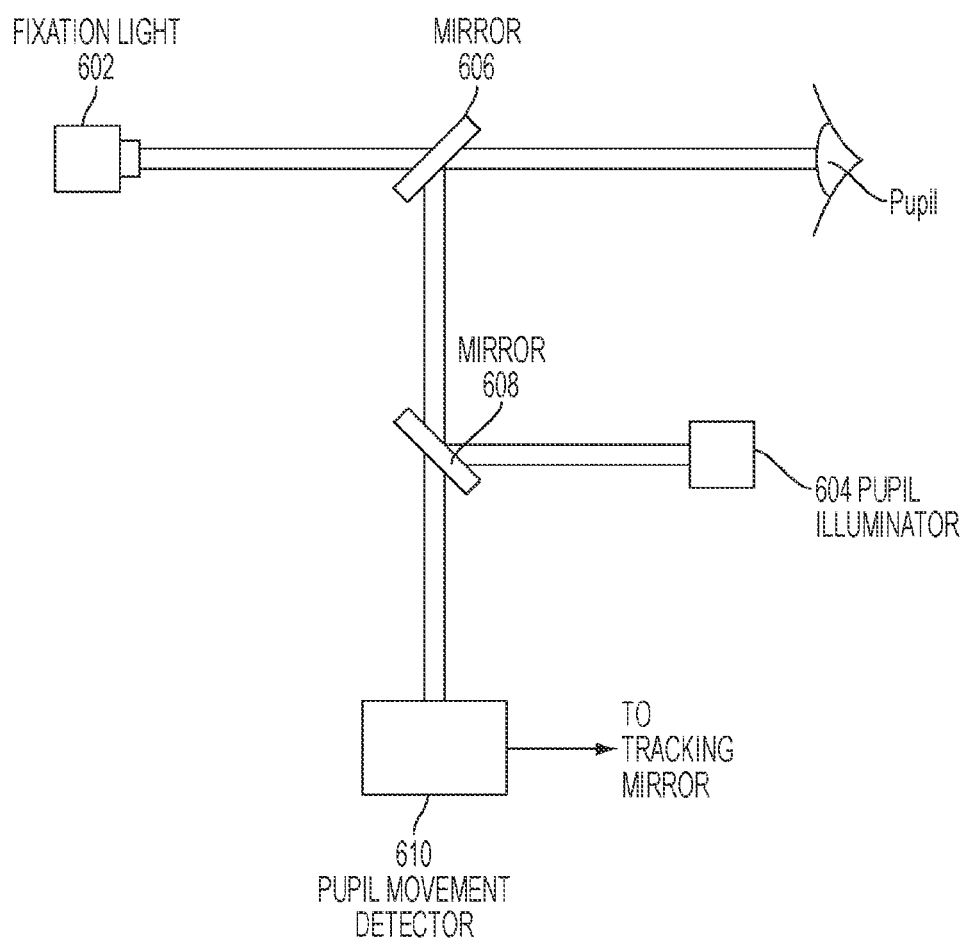
FIG. 6 is a schematic illustration of a simple eye tracking mechanism capable of compensating for eye movements.

FIG. 6 is a schematic illustration of a simple eye tracking mechanism 600 including a fixation light 602, pupil illuminator 604, mirrors 606 and 608 and pupil movement detector 610. Light from the illuminator 604 enters the eye and induce a reflection back through the pupil ("pupil glow") which can be monitored by the detector 610. When eye movement is detected a tracking signal can be sent to the tracking mirror, e.g., the tracking mirror 506 of FIG. 5, to compensate.

In another embodiment, the apparatus can also be a handheld automated device. The handheld automated device can comprise a light source and detector as described above. In one embodiment, the light source can be compact in size for use in the handheld device. In one embodiment, the detector can be a camera to capture two dimensional images. The camera can be a charge-coupled device. The camera can also be an intensified or electron multiplying camera.

The handheld device can further comprise an automated eye tracking mechanism to align (move) the irradiation position even if the tissue moves during illumination. Specifically, coupling the eye tracking mechanism with an automated response system which provides real-time beam adjustment, so that eye movements are nullified relative to the system. Accordingly, one embodiment comprises a method of tracking the movement of the eye by imaging the eye with the handheld automated device. The detector can comprise a camera and the movement of the eye can be tracked with reference points in the eye.

The handheld apparatus can also comprise a processor. The processor can calculate and quantify information received from two dimensional images obtained from the light source and detector. The processor can also control the camera by synchronizing with the light source to capture a series of temporal two-dimensional images of the tissue. Additionally, the processor can have an input/output control, memory, electronic circuitry made of digital circuitry, analog circuitry, or both and can be programmable. In one embodiment, the processor can be a microprocessor. The microprocessor can be programmed to synchronize image capture rate with the light source. Additionally, the microprocessor can synchronize image capture rate with the pulse monitor and the camera to obtain temporal two-dimensional images at specific time intervals during the cardiac cycle.

In another embodiment, information collected from the detector can be transmitted to a remote source such as a processor, computer, database, remote physician or the like via wireless information transfer or other connection through a suitable communication link or a computer network where the information can be converted from the two dimensional images, e.g. vessel and blood cell location, to quantifiable blood flow dynamic measurements.

The handheld apparatus can also comprise a scanner. The scanner can deflect the light to move across a section of the tissue or capture images from a particular coordinate or set of coordinates on the tissue. Some non-limiting examples of scanners for use with the handheld apparatus can be a galvanoscanner, a resonant mirror scanner, an acoustic optical modulator, a polygonal scanner and/or a microelectromechanical scanner. The light source can be directly connected to the scanner.

EXAMPLES

Conjunctiva blood flow (BF) was determined from a sequence of image frames in the following steps: 1) image registration, 2) blood vessel centerline extraction, 3) blood vessel diameter calculation, 4) axial red blood cell velocity derivation; 5) average cross-sectional blood velocity and BF calculation. A description of each step is given below. All software and analysis algorithms were written in Matlab (The Mathworks Inc. Natick, Mass.).

A Zeiss slit lamp biomicroscope equipped with a digital charged coupled device camera (UNIQVision Inc., Santa Clara, Calif.) was used to capture images of the human bulbar conjunctiva. A green filter with a transmission wavelength of 540±5 nm was placed in the path of the slit lamp illumination light to improve the contrast of blood vessels. The optics of the slit lamp and additional magnification optics placed in front of the camera magnified the image of conjunctiva blood vessels. The system was calibrated by capturing an image of a ruler placed at the image plane. The digital image was comprised of 1024×1024 pixels and each pixel on the image was equivalent to 0.7 microns. During image acquisition, a sequence of 62 images was acquired at a rate of 50 Hz. In one normal human subject, 3 sets of conjunctiva images were acquired from different locations. From each image set, 20 to 40 consecutive frames were selected for registration based on image focus and the absence of blinks or large eye movements.

Due to eye movement, features such as blood vessels do not remain stationary during image acquisition. Image registration is a necessary pre-processing step to compensate for eye motion and to put each image in a common reference frame. A semi-automated, area based image registration technique was employed. The first image frame of the image sequence served as the reference frame, and each subsequent image was registered to the reference frame. The registration procedure consisted of first identifying approximately 20-40 high contrast points (e.g. vessel intersections) in the first frame by hand. The reference points were identified by recording the row and column image locations of mouse clicks on the first image. Windows of 81×81 pixels, containing pixel intensity data of the image, were automatically centered on the row and column locations of each reference point. Correlation coefficients (CC) were computed between pixel intensity values in the reference frame windows and search windows in the non-registered frames to establish correspondence (similarity). Specifically, for each reference window, a corresponding search window was moved pixel by pixel in the non-registered image. At every location of the search window, a CC value was computed. The center location of the search window in the non-registered image that resulted in the largest CC (i.e. greatest similarity of pixel values between the reference and search windows) was assumed to be the location matching the reference point location. A sub-pixel matching algorithm (Gruen, 1985) was employed to improve the precision of the matched points locations to sub-pixel accuracy and increase the CC values. The sub-pixel matching routine used an iterative, non-linear least squares solution to shift the each search window in sub-pixel increments to minimize the intensity difference between the reference and search windows. Using all the row and column coordinates of reference and matched points with a CC>0.8, parameters of a conformal coordinate transformation were defined with a least squares solution. The conformal transformation accounts for image translation, rotation, and scale. Since eye motion only translated and rotated image features, a linear conformal transformation was considered appropriate. Using this procedure, a unique conformal transformation was established for each frame and used to register the frame to the reference frame.

Vessel centerlines were extracted by processing the mean image of the registered images. First, a polygonal region of interest (ROI) was selected by hand to include a target vessel. Adaptive local thresholding, a type of image segmentation in which different intensity thresholds are used for different regions in the image, was then applied to the ROI to create a binary image with the vessel assigned to one and all other features assigned to zero.

Several morphological steps were then utilized on the binary image to thin the vessel to a centerline. 1) Hole filling to eliminate any holes within the vessel after binarization. This consisted of a flood-fill operation on the binary image. The binary image was filled from the edges of the image until reaching the boundary of the vessel. Locations that could not be filled were identified as holes in the vessel and then subsequently filled. 2) Dilation followed by erosion to bridge unconnected vessel areas. Dilation consisted of extending the boundary of the vessel to connect areas of the vessel that were initially not connected. Erosion was then used to thin the vessel back to the original size while maintaining connectivity. 3) Thinning to reduce the vessel to a single line. Pixels were removed from the vessel boundary until the vessel was thinned to a minimal line. 4) Removal of isolated pixels to eliminate noise. Any object in the image that did not contain a user specified number of pixels was eliminated. 5) Selection of the longest continuous line and spur elimination to remove smaller erroneous branches of the centerline. The connection point of two line segments was determined and pixels corresponding to the smaller segment were removed.

The vessel centerline was divided into 5-pixel length segments. For each segment, linear regression analysis of the column and row coordinates of the centerline yielded a slope and offset defining the local direction of the vessel. A line perpendicular to the centerline, determined by computing the inverse of the slope, and extending beyond the vessel walls was defined. Two-dimensional bilinear interpolation was performed to obtain the intensity profile of the perpendicular line. The intensity profile was normalized between zero and one and the full-width at half maximum (FWHM) was computed. The vessel diameter was objectively and automatically quantified by the FWHM of the normalized intensity profile, a commonly used parameter for evaluation of vessel width in retinal images. (Patton, 2006) This procedure was repeated for each 5-pixel length centerline segment along the entire length of the vessel centerline. The vessel diameter was derived as the average of FWHM measurements.

Axial red blood cell (RBC) velocity ($V_a$) was measured by tracking the movement of RBCs along the vessel. Tracking of cells was accomplished using a technique, (Ellis, 1992; Japee, 2005, Japee, 2005) which was further advanced to provide quantitative measurements of RBC $V_a$. Tracking of cells involved creating a spatial-temporal image (STI) composed of the location of RBCs (spatial) as a function of the image frame (temporal). More succinctly, the STI is an image which contains the intensity data along the vessel as a function of time. The intensity data along the vessel was obtained by first averaging intensity data over the vessel diameter. For each pixel along the vessel centerline, a line perpendicular to the centerline with length equal to the vessel diameter was selected. The intensity values along the perpendicular line were averaged to obtain a mean intensity over the vessel diameter. The intensity data along the vessel was then stored in a column of the STI. This procedure was repeated for each registered image and the intensity data along the vessel was stored as a separate column of the STI. In this manner, the STI was created such that the columns represented time (image frame) and the rows represent the distance along the blood vessel.

The STI revealed distinct bands of low and high intensity, each corresponding to the movement of RBC columns or the space between them in the image sequence, respectively. To obtain $V_a$, a binary STI was created by thresholding of the grayscale STI. Pixels in the grayscale STI with intensity values above a threshold were assigned to one, while pixels below the threshold were assigned to zero. The bands assigned to one in the binary STI were sorted in order of the number of pixels they contained and the longest continuous bands (i.e. the bands containing the largest number of pixels) were selected. The slope of each band was determined using linear regression of the row and column coordinates of the pixels within the band. Since the slope of the bands represents a change of position of the RBC columns over a period of time, the slope is equivalent to the RBC velocity. The mean slope of the identified bands was a measure of $V_a$.

Cross sectional blood velocity, $V_s$, was calculated from $V_a$ using a previously defined function (Koutsiaris, 2007) that accounts for the diameter of the blood vessel (D) relative to the size of the human erythrocyte diameter (7.65 microns). This equation describes the change in the velocity profile with small vessel diameters and is appropriate for blood flow in capillaries. From $V_s$, the cross-sectional BF was determined using a standard flow rate equation: $BF = V_s \pi D^2 / 4$.

Figure 7:
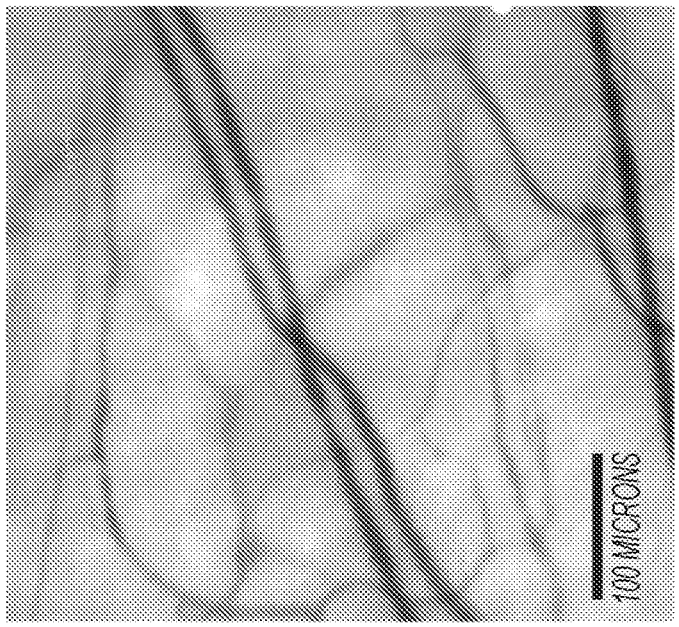
FIG. 7A shows an image of conjunctiva blood vessels derived by averaging 40 consecutive non-registered images.
FIG. 7B shows an image of conjunctiva blood vessels derived by averaging 40 consecutive registered images.
Figure 7:
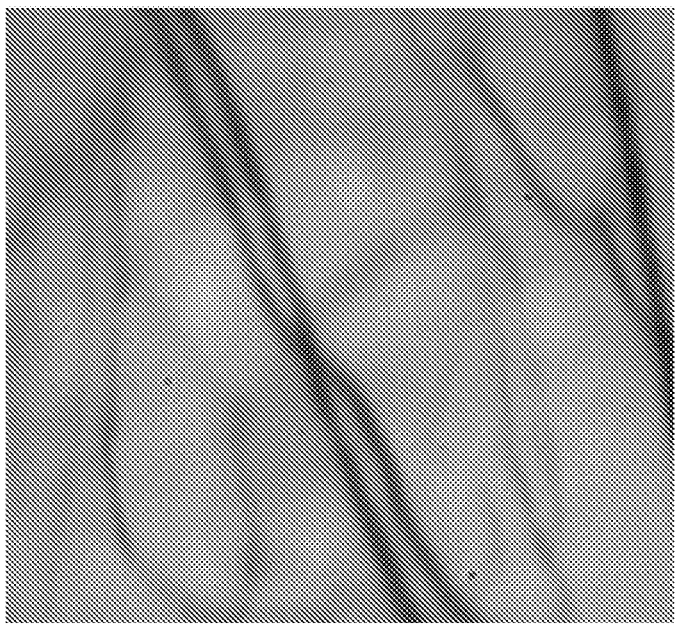

A typical example of the mean image of 40 consecutive non-registered images of the conjunctiva vasculature acquired in one image sequence is shown in FIG. 7A. Clearly, significant blurring occurs due to eye motion. Images were registered by selecting control points with high contrast in the first image frame (reference frame). FIG. 7B displays the mean of the registered images. Improvement in vessel sharpness is observed, which indicates correct image registration.

Figure 8:
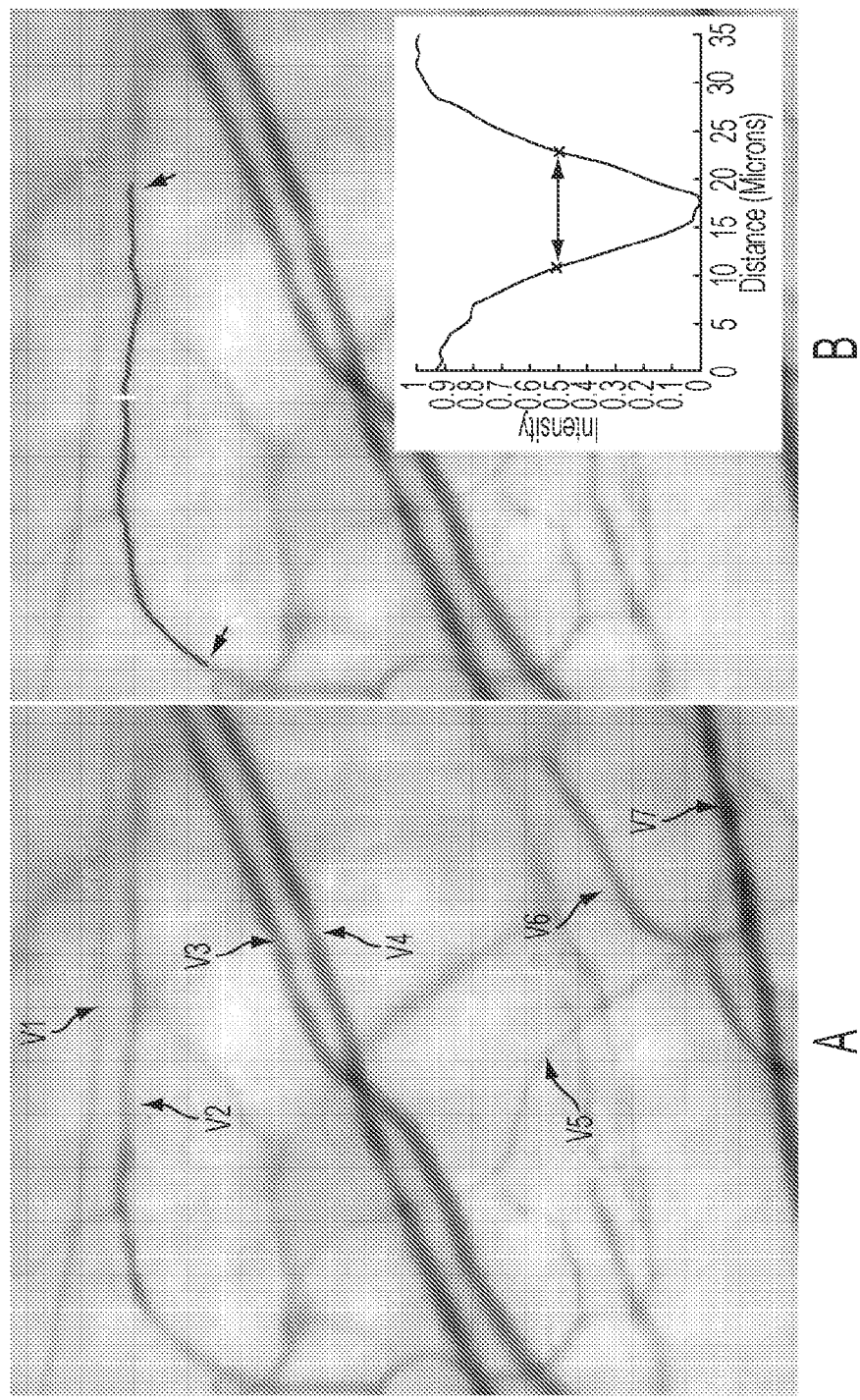
FIG. 8A shows seven blood vessels identified on the image.
FIG. 8B depicts the overlay of a center line on the blood vessel segment marked by arrows with the insert showing the intensity profile along the white line drawn perpendicular to the blood vessel center line.
Figure 9:
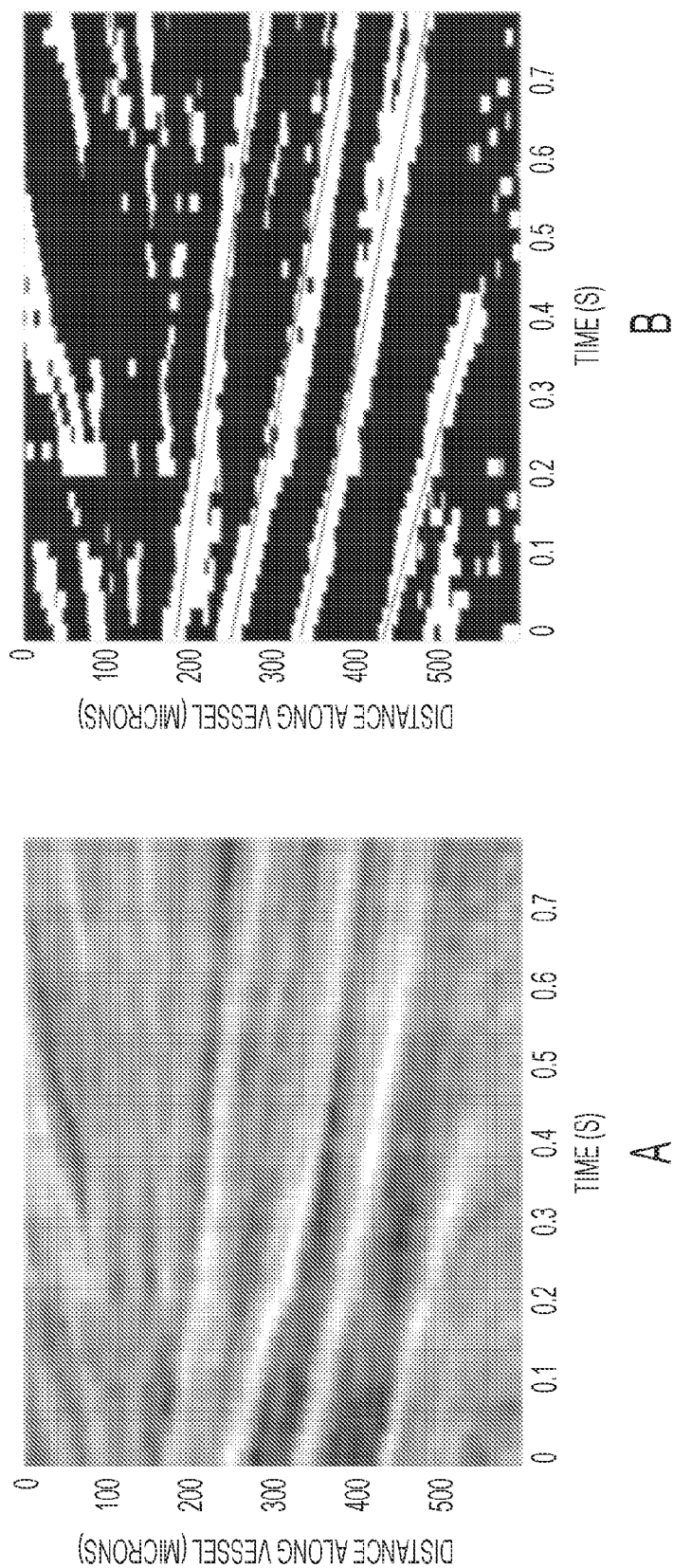
FIG. 9A shows a spatial-temporal image generated for the blood vessel V2 outlined in FIG. 8B.
FIG. 9B shows the best fit line to each continuous band on the binarized spatial-temporal image is displayed.

A registered mean conjunctiva vasculature image depicting seven blood vessels is shown in FIG. 8A. As an example, the overlay of the computed blood vessel centerline on the blood vessel V2 is shown in FIG. 8B. The full width at half-maximum of the intensity profile is a measure of blood vessel diameter. From the normalized intensity profile of the line perpendicular to the blood vessel centerline, the FWHM was calculated as a measure of blood vessel diameter. Multiple measurements were made along a blood vessel V2, yielding a mean blood vessel diameter of 13.1±3.7 microns (N=156). FIG. 9A displays an example of a STI generated for blood vessel V2 (FIG. 8B). The vertical and horizontal axes represent distance along the vessel length and time, respectively. The pixel values represent the intensity values at a given distance along the vessel and frame time. The best fit lines to each continuous band on the binarized STI are shown (FIG. 9B). The line slope is a measure of axial blood velocity. Each band represents tracking of RBCs and its slope is a measure of axial RBC velocity, $V_a$. The average $V_a$ in blood vessel V2 was 0.31±0.13 mm/sec (N=4).

Figure 10:
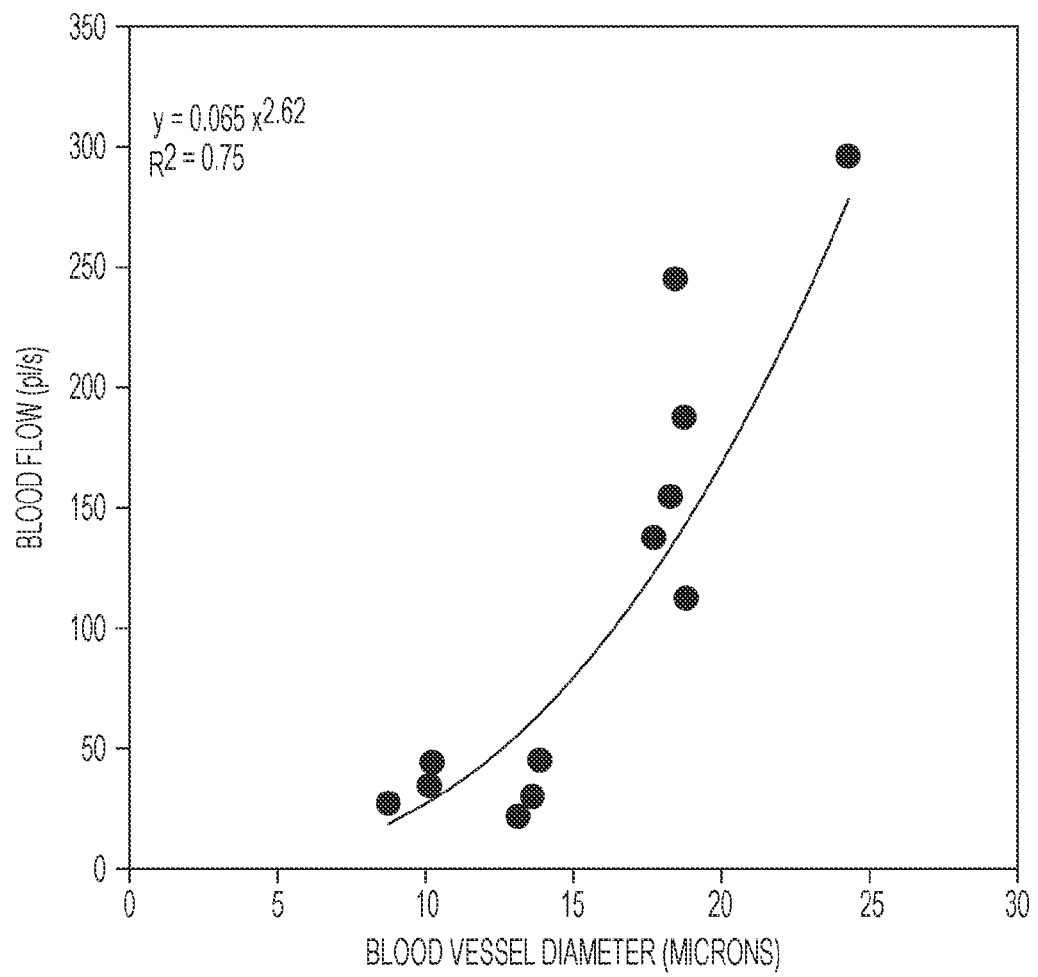
FIG. 10 shows the relationship between blood flow rate and vessel diameter (N=12)

Blood vessel diameter and cross sectional blood velocity measurements were obtained in 12 blood vessels from 3 image sequences. A summary of blood vessel diameter and axial velocity measurements is shown in Table 1. Blood vessels had diameters ranging between 8.7 and 24.3 microns, with a mean value of 15.5 microns. On average, the standard error of the mean (SEM) for blood vessel diameter measurements was 0.3 microns and the coefficient of variation (COV) was 19% (3 microns) (N=12). Cross sectional blood velocities ranged between 0.2 and 1.2 mm/sec, with a mean value of 0.7 mm/sec. The COV for cross sectional blood velocity measurements was on average 18%, ranging between 4% and 36% (N=12). The relationship between flow rate and blood vessel diameter is shown in FIG. 10. Blood flow rate ranged between 27.3 and 296.9 pl/s, with a mean value of 111.8 pl/s. The best fit curve to the flow rate data was a power law curve ($Q = 0.065 D^{2.62}$), displaying a high correlation (R=0.87).

TABLE 1

Mean and standard error of the mean (SEM) of blood vessel diameter and axial velocity measurements.

| Vessel | Diameter (microns) | | | Axial Velocity (mm/sec) | | |
|---|---|---|---|---|---|---|
| | Mean | SEM | N | Mean | SEM | N |
| V1 | 10.2 | 0.4 | 87 | 1.1 | 0.1 | 4 |
| V2 | 13.1 | 0.3 | 156 | 0.3 | 0.1 | 4 |
| V3 | 18.3 | 0.4 | 176 | 1.1 | 0.1 | 3 |
| V4 | 17.7 | 0.2 | 183 | 1.0 | 0.1 | 3 |
| V5 | 8.7 | 0.2 | 33 | 0.9 | 0.1 | 4 |
| V6 | 13.8 | 0.2 | 46 | 0.6 | 0.1 | 3 |
| V7 | 18.4 | 0.2 | 109 | 1.6 | 0.1 | 2 |
| V8 | 10.1 | 0.4 | 59 | 0.8 | 0.2 | 2 |
| V9 | 13.6 | 0.2 | 79 | 0.4 | 0.1 | 5 |
| V10 | 18.7 | 0.1 | 179 | 1.2 | 0.2 | 3 |
| V11 | 18.8 | 0.2 | 154 | 0.7 | 0.1 | 2 |
| V12 | 24.3 | 0.4 | 44 | 1.1 | 0.3 | 2 |

Figure 11:
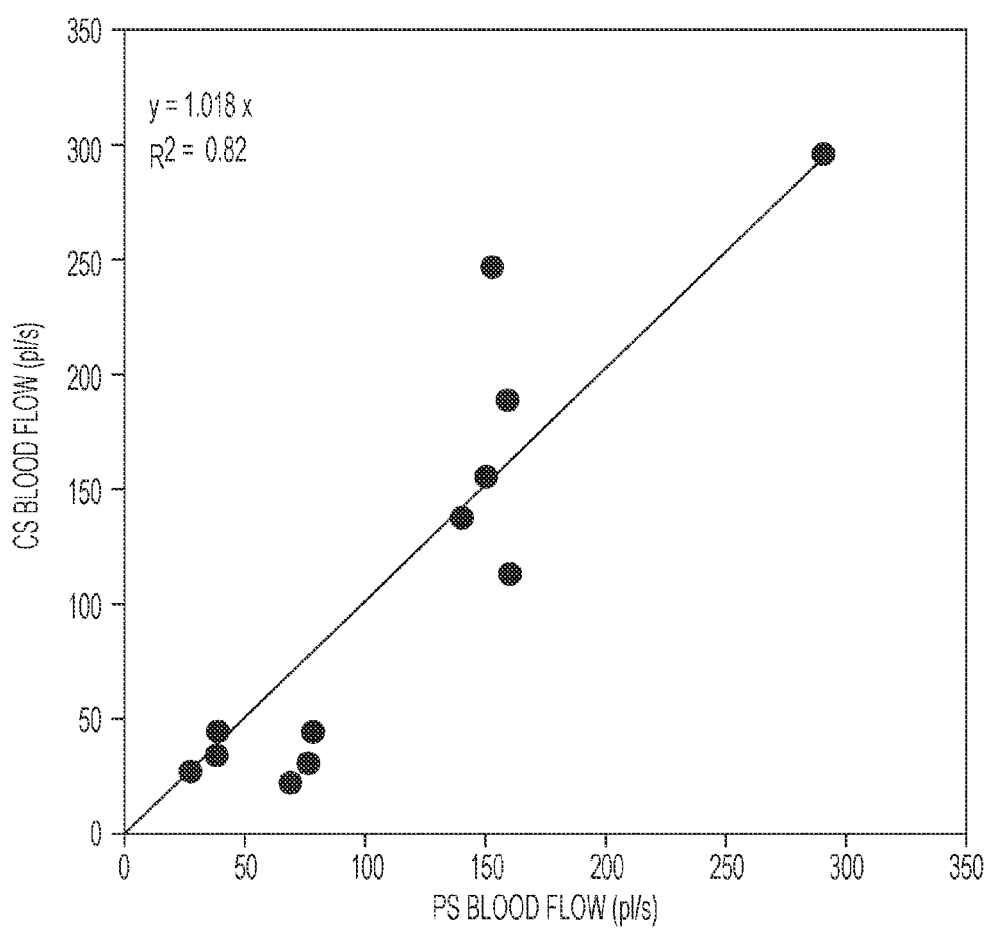
FIG. 11 shows the relationship between blood flow estimated by the power law curve derived in the current study (CS) and in a previous study (PS).

Blood flow rate measurements were related to blood vessel diameter following a power law curve. In FIG. 11, flow rates estimated from the power law curve is plotted as function of flow rates estimated using the power law curve derived from a previous study (Koutsiaris, 2007). Linear regression analysis yielded a best fit line with slope of 1.02 and a very high correlation (R=0.91).

One skilled in the art will appreciate further features and advantages of the invention based on the above-described embodiments. By way of non-limiting example, the devices and methods of the present invention can employ blood flow dynamic measurements related to blood vessel parameters. Accordingly, the invention is not to be limited by what has been particularly shown and described, except as indicated by the appended claims. All patents, publications and references cited herein are expressly incorporated herein by reference in their entirety.

What is claimed is:

1. A method for determining blood velocity in a conjunctiva of an eye, comprising:
   acquiring a series of temporal frames with registered images of at least one vessel in the conjunctiva of the eye, wherein the registered images are registered to compensate for eye motion;
   identifying at least one blood cell present in each of a plurality of frames;
   calculating blood velocity within the vessel based on a distance travelled by the blood cell in the vessel between frames; and
   compensating for involuntary target movement by tracking eye movements.

2. The method of claim 1, wherein the step of acquiring the images further comprises illuminating the conjunctiva of the eye with light having a wavelength in a range of about 500 nm to 560 nm.

3. The method of claim 1 further comprising determining blood flow in the blood vessel by:
   obtaining a two-dimensional image of the vessel in the conjunctiva of the eye;
   determining dimensions of the vessel from the two-dimensional image; and
   calculating blood flow within the vessel based on blood cell velocity and blood vessel dimensions.

4. A hemodynamics measurement apparatus comprising:
   a light source configured to project radiation onto a target tissue;
   optics configured to image at least one vessel in the tissue;
   a detector to capture a series of temporal images of the vessel;
   a processor to calculate blood flow dynamics in the vessel from the series of images; and
   an eye tracking mechanism that compensates for involuntary movement of the eye from one temporal image to another,
   wherein the apparatus is configured to image at least one blood vessel in the conjunctiva of a subject's eye.

5. The apparatus of claim 4, wherein the apparatus further comprises a biomicroscope.

6. The apparatus of claim 4, wherein the light source generates light of at least one wavelength in the range of about 450 to 600 nm.

7. The apparatus of claim 6, wherein the light source generates light at a wavelength in a range from about 500 nm to about 600 nm.

8. The apparatus of claim 7, wherein the light source generates light at a wavelength in a range from about 500 nm to about 560 nm.

9. The apparatus of claim 4, wherein the eye tracking mechanism is configured to detect changes in pupil position.

10. The apparatus of claim 4, wherein the detector comprises a camera.

11. The apparatus of claim 10, wherein the camera is a charge-coupled device (CCD).

12. The apparatus of claim 10, wherein the apparatus further comprises a camera controller configured to acquire a plurality of images over a time interval.

13. The apparatus of claim 12, wherein the camera controller is configured to acquire images at least 40 Hz.

14. The apparatus of claim 4, wherein the detector is configured to acquire two-dimensional images.

15. The apparatus of claim 4, wherein the apparatus is a handheld apparatus.

* * * * *